(12) United States Patent
Bouvier et al.

(10) Patent No.: US 12,193,860 B2
(45) Date of Patent: *Jan. 14, 2025

(54) IMAGING SYSTEM WITH CARBON FIBER C-ARM

(71) Applicants: GE Precision Healthcare LLC, Waukesha, WI (US); IRT JULES VERNE, Bouguenais (FR)

(72) Inventors: Bernard Bouvier, Eragny (FR); François Kotian, Villepreux (FR); Carlos Martinez Ferreira, Paris (FR); Camille Sébastien, Nantes (FR); Stéphanie Colliou, Carquefou (FR); Matthieu Kneveler, Pont Saint Martin (FR)

(73) Assignees: GE Precision Healthcare LLC, Waukesha, WI (US); IRT Jules Verne, Bouguenais (FR)

( * ) Notice: Subject to any disclaimer, the term of this patent is extended or adjusted under 35 U.S.C. 154(b) by 0 days.

This patent is subject to a terminal disclaimer.

(21) Appl. No.: 18/526,590

(22) Filed: Dec. 1, 2023

(65) Prior Publication Data
US 2024/0099680 A1 Mar. 28, 2024

Related U.S. Application Data

(63) Continuation of application No. 17/351,727, filed on Jun. 18, 2021, now Pat. No. 11,864,938.

(51) Int. Cl.
  *A61B 6/00* (2024.01)
  *A61B 6/46* (2024.01)
  *G06T 11/00* (2006.01)

(52) U.S. Cl.
  CPC ............ *A61B 6/4441* (2013.01); *A61B 6/461* (2013.01); *G06T 11/003* (2013.01)

(58) Field of Classification Search
  None
  See application file for complete search history.

(56) References Cited

U.S. PATENT DOCUMENTS 11,864,938 B2 * 1/2024 Bouvier ............... A61B 6/461

* cited by examiner

*Primary Examiner* — David P Porta
*Assistant Examiner* — Mamadou Faye

(57) ABSTRACT

The present disclosure relates to a C-shaped arm for use with a medical imaging system. In accordance with certain embodiments, the C-shaped arm comprises a C-shaped portion, a radiation source carried by the C-shaped portion, and a radiation detector carried by the C-shaped portion, wherein at least a portion of the C-shaped portion is formed of a unidirectional ultra-high modulus carbon fiber material.

20 Claims, 10 Drawing Sheets

IMAGING SYSTEM WITH CARBON FIBER C-ARM

CROSS REFERENCE TO RELATED APPLICATIONS

The present application is a continuation of U.S. patent application Ser. No. 17/351,727, filed on Jun. 18, 2021, the disclosure of which is incorporated herein by reference in its entirety.

TECHNICAL FIELD

This disclosure relates to an imaging system with a C-arm and more particularly to a medical imaging system with a carbon fiber C-arm.

BACKGROUND

Radiographic medical imaging systems may provide non-invasive means for imaging internal structures (i.e., bone, tissue, etc.) of a patient. A radiographic imaging device may include a C-arm coupled to a base that supports the C-arm, a radiation source, and a radiation detector. The C-arm supports the radiation source and the radiation detector opposite the radiation source. The C-arm rotates about an examination region that includes a portion of the patient and the radiation source emits radiation that traverses the examination region. The radiation detector detects the radiation that traverses the examination region and generates a signal indicative thereof. A reconstructor processes the signal and reconstructs image data indicative of the examination region and the portion of the patient within the examination region.

SUMMARY

In one embodiment, the present disclosure provides a C-shaped arm for use with a medical imaging system comprising a C-shaped portion, a radiation source carried by the C-shaped portion, and a radiation detector carried by the C-shaped portion, wherein at least a portion of the C-shaped portion is formed of a unidirectional ultra-high modulus carbon fiber material.

In another embodiment, the present disclosure provides a medical imaging system comprising a C-arm, a radiation source and a radiation detector carried by the C-arm, a base, an extended portion coupled to the C-arm and the base, wherein the C-arm is configured at least 220° about an examination region.

In yet another embodiment, the present disclosure provides a method comprising acquiring first projection data with a medical imaging system that includes a C-arm that carries a radiation source and a detector, wherein the C-arm is at a first position when the medical imaging system acquires the first projection data, wherein a portion of the C-arm is formed of a unidirectional ultra-high modulus carbon fiber material, rotating the C-arm to a second position, acquiring second projection data with the medical imaging system when the C-arm is at the second position, reconstructing an image form at least one of the first projection data and the second projection data, and displaying the reconstructed image.

BRIEF DESCRIPTION OF THE DRAWINGS

Various aspects of this disclosure may be better understood upon reading the following detailed description with reference to the drawings in which.

Figure 1:
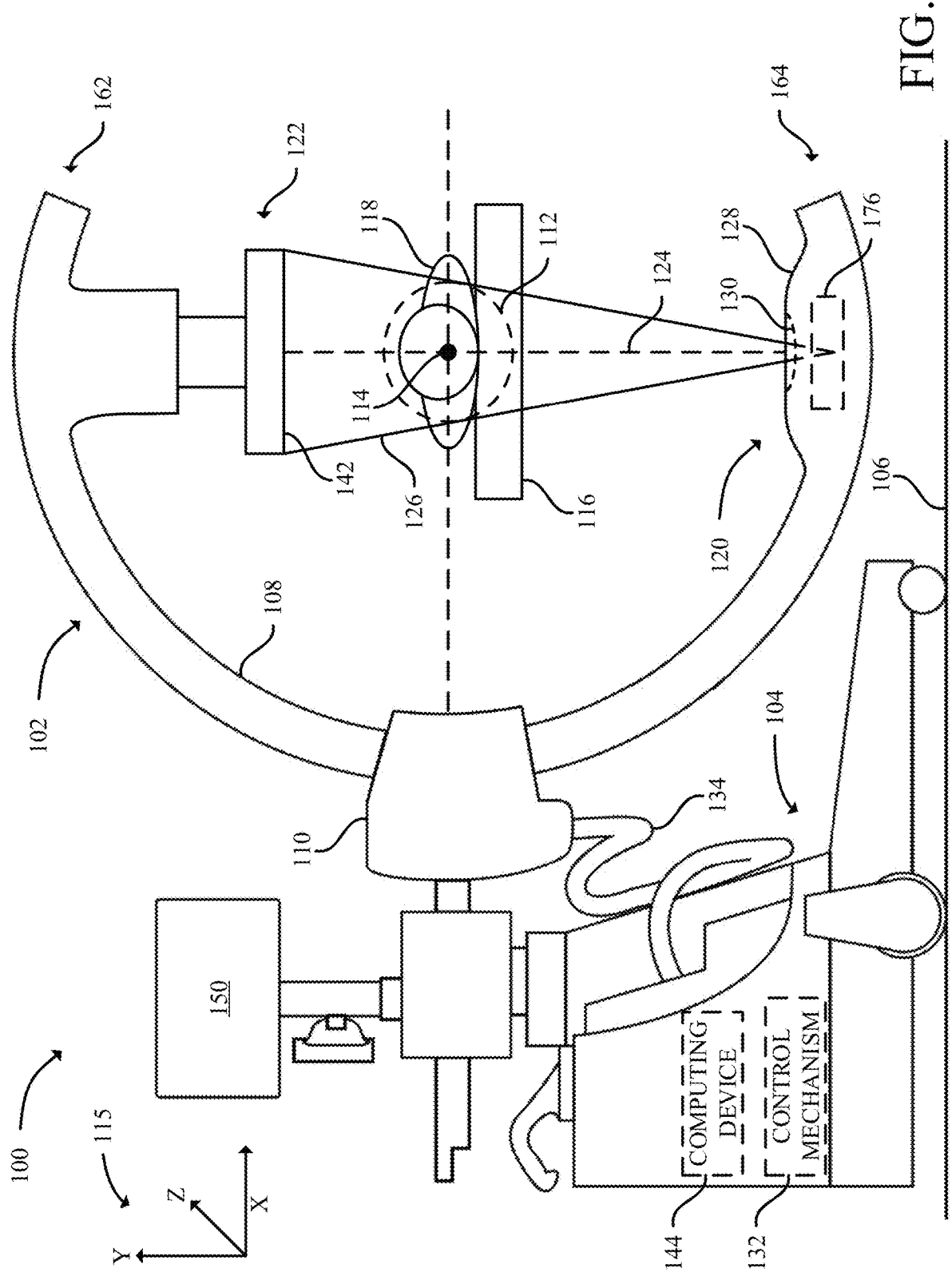
FIG. 1 depicts a medical imaging system in accordance with an exemplary embodiment.

The drawings illustrate specific acts of the described components, systems, and methods for a medical imaging system with a carbon fiber C-arm. Together with the following description, the drawings demonstrate and explain the structures, methods, and principles described herein. In the drawings, the thickness and size of components may be exaggerated or otherwise modified for clarity. Well-known structures, materials, or operations are not shown or described in detail to avoid obscuring aspects of the described components, systems, and methods.

DETAILED DESCRIPTION

One or more specific embodiments of the present disclosure are described below. These described embodiments are only examples of the systems and methods for a medical imaging system with a carbon fiber C-arm. The skilled artisan will understand that specific details described in the embodiments can be modified when being placed into practice without deviating from the spirit of the present disclosure.

When introducing elements of various embodiments of the present disclosure, the articles "a," "an," and "the" are intended to mean that there are one or more of the elements. The terms "first," "second," and the like, do not denote any order, quantity, or importance, but rather are used to distinguish one element from another. The terms "comprising," "including," and "having" are intended to be inclusive and mean that there may be additional elements other than the listed elements. As the terms "connected to," "coupled to," etc. are used herein, one object (i.e., a material, element, structure, number, etc.) can be connected to or coupled to another object regardless of whether the one object is directly connected or coupled to the other object or whether there are one or more intervening objects between the one object and the other object. In addition, it should be understood that references to "one embodiment" or "an embodiment" of the present disclosure are not intended to be interpreted as excluding the existence of additional embodiments that also incorporate the recited features.

Medical imaging systems may include a C-shaped arm that carries a radiation source and a radiation detector. The C-shape of the arm allows a physician to access to a patient while the patient is being imaged. In order to obtain medical images of an internal structure at various angles, the C-shaped arm may be rotated to various positions. However, an amount the C-shaped arm may be rotated may limited by a structural strength of the C-shaped arm. Stated another way, vibration may irreversibly deform the C-shaped arm if the C-shaped arm is rotated beyond a given rotational angle. Some embodiments of the present disclosure relate to a C-shaped arm of a medical imaging system formed at least in part of a carbon fiber material. Providing a C-shaped arm formed at least in part of a carbon fiber material may increase a structural strength of the C-shaped arm which may allow this C-shaped arm to rotate farther than other C-shaped arms made of other materials.

Furthermore, movement produced by the radiation source while the radiation source is emitting radiation may cause the C-shaped arm to vibrate. This vibration may cause an unwanted image artifact within a medical image acquired by the medical imaging system. Providing a C-shaped arm formed at least in part of a carbon fiber material may reduce an amount the C-shaped arm vibrates due to the increased structural strength of the arm, mechanical properties of the arm (i.e., stiffness), and geometry of the arm which influence vibration characteristics (i.e., frequency, amplitude, and dampening) thereby reducing an amount of image artifacts within images produced by the medical imaging system with this C-shaped arm.

The following description relates to various embodiments for a medical imaging system with a C-arm. A medical imaging system, such as the medical imaging system shown in FIG. 1, includes a C-arm configured to rotate around at least one rotational axis. The C-arm includes a radiation source and a radiation detector at opposite ends of the C-arm.

Referring to the figures generally, the present disclosure describes systems and methods for a medical imaging system with a carbon fiber C-arm. The medical imaging system described herein (i.e., the medical imaging system depicted in FIG. 1) may be generally referred to as a radiographic medical imaging system.

Referring now to FIG. 1, a medical imaging system 100 is shown in accordance with an exemplary embodiment. The medical imaging system 100 includes a rotatable C-arm 102 that is connected to a base 104. The base 104 supports the C-arm 102 while the C-arm 102 is stationary and while rotating. The base 104 supports the C-arm 102 on a ground surface 106 on which the medical imaging system 100 sits. The C-arm 102 includes a C-shaped portion 108 that is connected to an extended portion 110. The C-shaped portion 108 may be formed of a composite material, such as carbon fiber fabric. The carbon fiber fabric may provide increased strength to the C-shaped portion 108 and/or a reduced weight of the C-shaped portion 108 relative to C-arms that include a C-shaped portion formed of a different material (i.e., steel, aluminum, etc.). The extended portion 110 is rotatably coupled to the base 104 which allows the C-arm 102 to rotate about an examination region 112 and a rotational axis 114. For example, the C-arm 102 may be configured to rotate at least 180° in opposing directions relative to the base 104. As will be discussed in further detail herein, in some embodiments, the C-arm 102 may be configured to rotate at least 220°. Configuring the C-arm 102 to rotate at least 220° may provide a physician with greater access to a patient being imaged. Structural characteristics (i.e., material used to form the C-shaped portion 108) may reduce an amount of vibration and deformation the C-arm 102 experiences when the C-arm 102 rotates about the rotational axis 114. While the following describes the rotation of the C-arm 102 as rotating in the X and Y directions of the Cartesian coordinate system 115 (i.e., rotating the C-shaped portion 108 such that opposing ends of the C-shaped portion 108 are closer to or further from the extended portion 110 in various positions), it is understood that the C-arm 102 may also rotate in the Z direction (i.e., rotating the C-shaped portion 108 such that opposing ends of the C-shaped portion 108 are closer to or further from a head of the patient within the examination region 112 in various positions).

The medical imaging system 100 further includes a patient support 116 (i.e., couch, bed, table, etc.) that supports a patient 118 while at least a portion of the patient 118 is within the examination region 112. The medical imaging system 100 additionally includes a radiation source 120 and a radiation detector 122. The radiation source 120 and the radiation detector 122 are supported by and rotate with the C-arm 102. Furthermore, the radiation source 120 and the radiation detector 122 are positioned at opposite ends of the C-shaped portion 108 of the C-arm 102 along axis 124, where axis 124 intersects and extends radially relative to the rotational axis 114. The C-shaped portion 108 may be rotated as described above in order to adjust the position of the radiation source 120 and the radiation detector 122. Furthermore, in the embodiment depicted in FIG. 1, the position of the radiation detector 122 may be varied such that the radiation detector 122 is placed further from or closer to the radiation source 120.

During a medical imaging procedure, a portion of the patient 118 is within the examination region 112 and the radiation source 120 emits radiation 126. In one embodiment, the radiation source 120 may include an X-ray tube (not shown in FIG. 1) housed within a casing 128. The X-ray tube generates the radiation 126 which escapes the casing 128 via an outlet 130. The radiation 126 traverses the examination region 112 and is attenuated by the portion of the patient 118 that is within the examination region 112. Specifically, the radiation source 120 emits the radiation 126 towards the radiation detector 122 which is on the opposite end of the C-arm 102. The radiation source 120 emits cone-shaped radiation which is collimated to lie within an X-Y-Z plane of the Cartesian coordinate system 115 which is generally referred to as an "object plane" which is parallel to the radiation detector 122 at an isocenter of the C-arm 102.

After passing through a portion of the patient 118, the attenuated radiation is captured by the radiation detector 122. In some embodiments, the radiation detector 122 includes a plurality of detector elements (not shown) that acquire projection data. Each detector element produces an electrical signal that is a measurement of the attenuation at the detector element location. The attenuation measurements from all the detector elements in the detector 122 are acquired separately to produce a transmission profile. In one embodiment, the radiation detector 122 is fabricated in a flat panel configuration including a plurality of detector elements.

When the radiation source 120 and the radiation detector 122 are rotated with the C-arm 102 within the object plane and around the patient 118, the angle at which the radiation 126 intersects the patient 118 changes. A group of attenuation measurements (i.e., projection data) form the radiation detector 122 at one C-arm angle is referred to a "view." A "scan" of the patient 118 includes asset of views made at different angles, or view angles, during rotation of the C-arm 102. As used herein, the term view is not limited to the use described herein with respect to projection data from one C-arm 102 angle. The term view is used to mean one data acquisition whenever there are multiple acquisitions from different angles.

The medical imaging system 100 further includes a control mechanism 132 that is housed within the base 104. The control mechanism 132 is connected to the C-arm 102, the radiation source 120, and the radiation detector 122 via a cable 134 which allows the control mechanism to send data to/receive data from the C-arm 102, the radiation source 120, and the radiation detector 122. The control mechanism 132 controls the rotation of the C-arm 102 and the operation of the radiation source 120. Briefly turning to FIG. 2, a block diagram of the control mechanism 132 is shown in accordance with an exemplary embodiment. In one embodiment, the control mechanism 132 includes a radiation source controller 136 and a C-arm motor controller 138. The radiation source controller 136 is configured to provided power and timing signals to the radiation source 120. The C-arm motor controller 138 is configured to control a rotation speed and/or position of the C-arm 102. Furthermore, the C-arm motor controller controls the rotation axis of the C-arm 102, a position of the detector 122 and thereby controlling a source to detector distance, and a location of the patient support 116. The control mechanism 132 further includes a data acquisition system (DAS) 140. The DAS 140 is configured to sample analog data received from the radiation detector 122 and convert the analog data to digital signals for subsequent processing. While FIG. 1 depicts the base 104 as including the control mechanism 132, in other embodiments the control mechanism may be separate from the base 104 (i.e., in a different room).

The C-arm 102 may be adjusted to a plurality of different positions by rotation of the C-shaped portion 108. For example, in an initial, first position shown by FIG. 1, the radiation detector 122 may be positioned vertically above the radiation source 120 relative to the surface 106 on which the medical imaging system 100 sits, with axis 124 arranged normal to the surface 106 intersecting a midpoint of the outlet 130 of the radiation source 120 and a midpoint of a detector surface 142 of the radiation detector 122. The C-arm motor controller 138 and a guide system within the extended portion 110 may adjust the C-shaped portion 108 from the first position to a different second position by rotating the C-shaped portion 108 via a coupling between the guide system and the C-shaped portion 108. In one example, the second position may be a position in which the radiation source 120 and the detector 122 are rotated 180° together relative to the first position such that the radiation source 120 is positioned vertically above the radiation detector 122, with the axis 124 intersecting the midpoint of the outlet 130 of the radiation source 120 and the midpoint of the detector surface 142 of the radiation detector 122. When adjusted to the second position, the radiation source 120 may be positioned vertically above the rotational axis 114 of the C-shaped portion 108 and the radiation detector 122 may be posited vertically below the rotational axis 114.

The medical imaging system 100 further includes a computing device 144 that is housed within the base 104. While FIG. 1 depicts the computing device 144 as housed within the base 104, in other embodiments the computing device 144 may be remote from the rest of the medical imaging system 100. As used herein, a computing device (or system) is any device/system capable of processing, storing, and/or transmitting data (i.e., tablet, handheld device, smartphone, personal computer, laptop, network computer, server, mobile communication device, etc.). The computing device 144 may be connected to a network (i.e., a wide area network (WAN), a local area network (LAN), a public network (the internet), etc.) which allows the computing device 144 to communicate with other devices on a same network. In some embodiments, the network may be regarded as a private network and may include, for example, a virtual private network.

Figure 3:
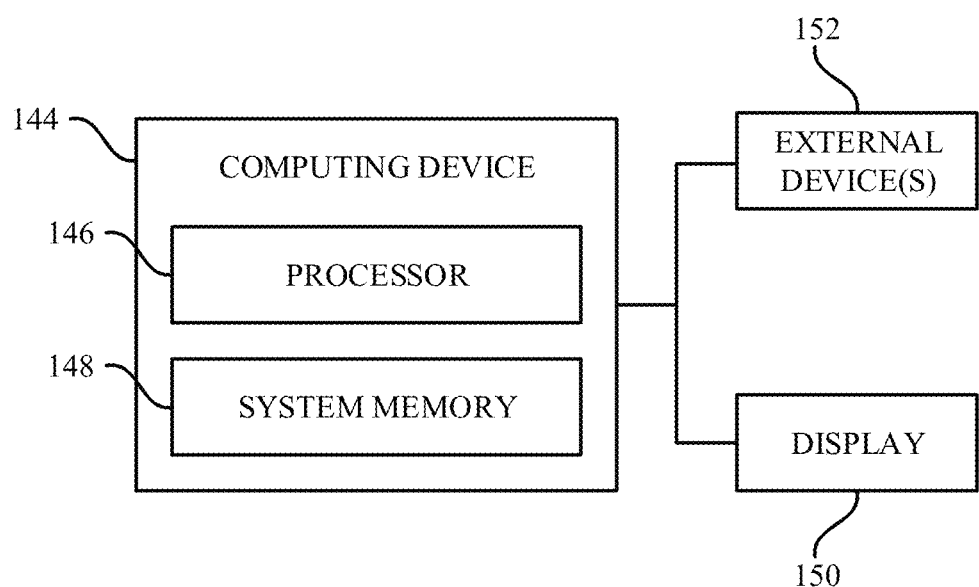
FIG. 3 is a is a block diagram of a computing device of a medical imaging system in accordance with an exemplary embodiment.

Briefly turning to FIG. 3, a block diagram of the computing device 144 is shown in accordance with an exemplary embodiment. The computing device 144 includes a processor 146 and a system memory 148. In some embodiments, the computing device is connected to a display 150 and one or more external devices 152. The processor 146 is in communication with the system memory 148 and may execute computer readable program instructions stored in the system memory 148. As used herein, a processor may include a central processing unit (CPU), or other electronic components capable or executing computer readable program instructions (i.e., a digital signal processor, a field-programmable gate array (FPGA), a graphics processing unit (GPU), etc.). Furthermore, as used herein, a processor may include two or more of a CPU, a digital signal processor, an FPGA, and a GPU.

The system memory 148 is a computer readable storage medium. As used herein, a computer readable storage medium is any device that stores computer readable program instructions for execution by a processor and is not construed as transitory per se. Computer readable program instructions include programs, logic, data structures, modules, etc. that when executed by a processor create a means for implementing functions/acts. Computer readable program instructions when stored in a computer readable storage medium and executed by a processor direct a computer system and/or another device to function in a particular manner such that a computer readable storage medium comprises an article of manufacture. System memory as used herein includes volatile memory (i.e., random access memory (RAM) and dynamic RAM (DRAM)) and non-volatile memory (i.e., flash memory, read-only memory (ROM), magnetic computer storage devices, etc.). In some embodiments the system memory 148 may further include cache.

In one embodiment, the various methods and processes (i.e., the method described below with reference to FIG. 13) may be stored as computer readable program instructions in the system memory 148. In this embodiment, the system memory 148 includes computer readable program instructions for imaging a patient with a medical imaging system (i.e., the medical imaging system 100).

The external devices 152 include devices that allow a user to interact with/operate the computing device 144 (i.e., mouse, keyboard, touchscreen, speakers, etc.). In some embodiments, the display 150 displays a graphical user interface (GUI). The GUI includes editable fields for inputting data (i.e., patient data, imaging parameters, etc.) and further includes selectable icons. Selecting an icon and/or inputting data causes the processor 146 to execute computer readable program instructions stored in the system memory 148 which causes the processor to perform a task. For example, a user of the computing device 144 may use an external device 152 to select a "start" icon or the like which causes the processor 146 to being a medical imaging procedure.

While FIG. 1 illustrates only one computing device 144, in some embodiments, the medical imaging system 100 may include more than one computing device 144. The computing device 144 may be used for inputting or outputting imaging parameters, requesting examinations, plotting data, and/or viewing images. Furthermore, in certain embodiments, the medical imaging system 100 may be coupled to multiple displays, printers, workstations, and/or similar devices located either locally or remotely (i.e., within an institution or hospital or in a an entirely different location, etc.) via one or more configurable wired and/or wireless networks. Furthermore, in some embodiments, the base further house an internal power source (not shown) that provides electrical power to operate the medical imaging system 100. Alternatively, the base 104 may be connected to an external power source to power the medical imaging system 100. A plurality of connection cables may (i.e., cable 134) may be provided to transmit electrical power to the radiation source 120, the radiation detector 122, etc.

The computing device 144 is in communication with and provides commands to the radiation source controller 136, the C-arm motor controller 138, and the DAS 140 for controlling system operations such as data acquisition and/or data processing. In some embodiments, the computing device 144 controls operation of the radiation source controller 136, the C-arm motor controller 138, and the DAS 140 based on a user input.

Figure 4:
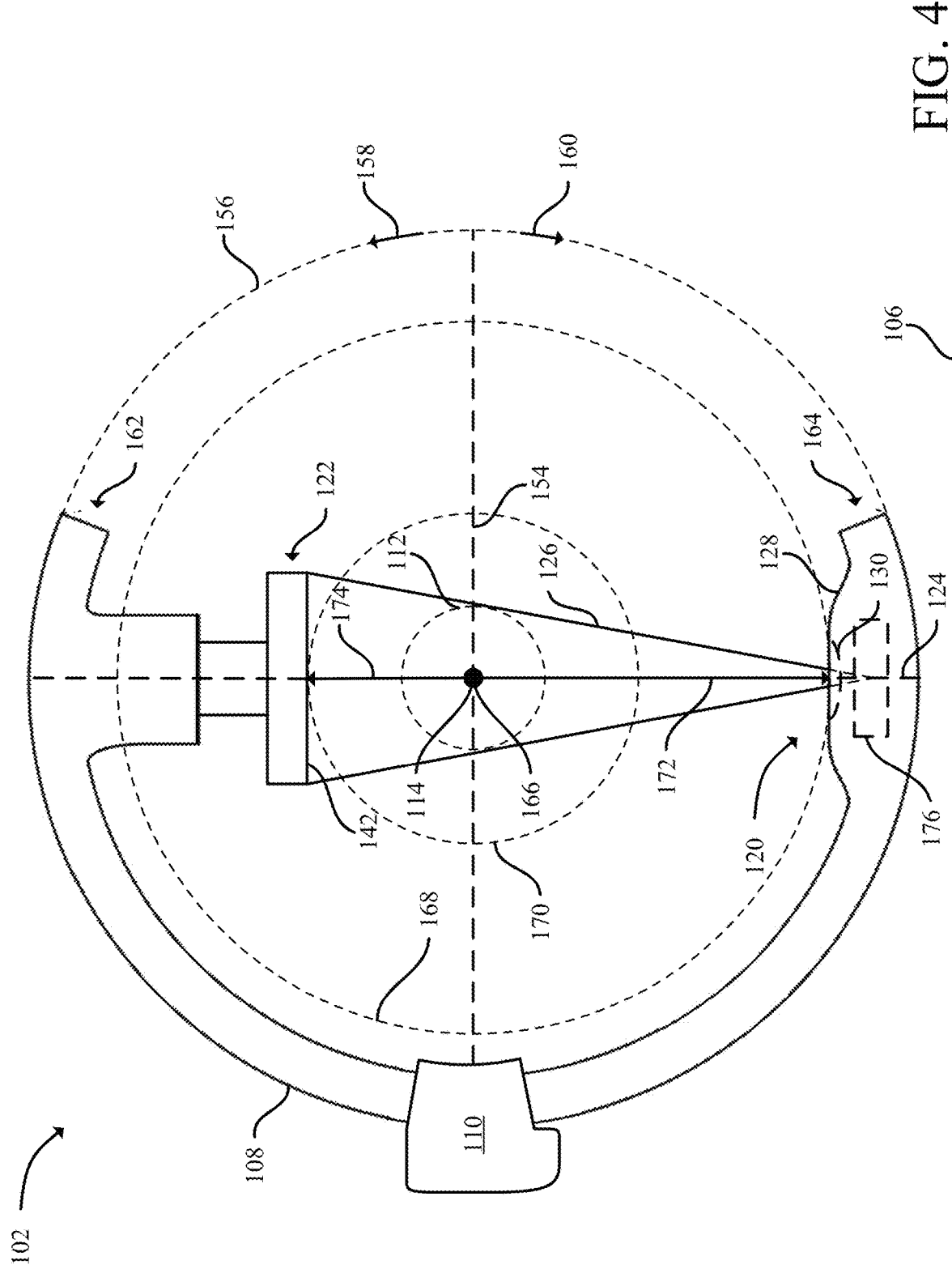
FIG. 4 is a schematic diagram of a C-arm of a medical imaging system in a first position in accordance with an exemplary embodiment.
Figure 6:
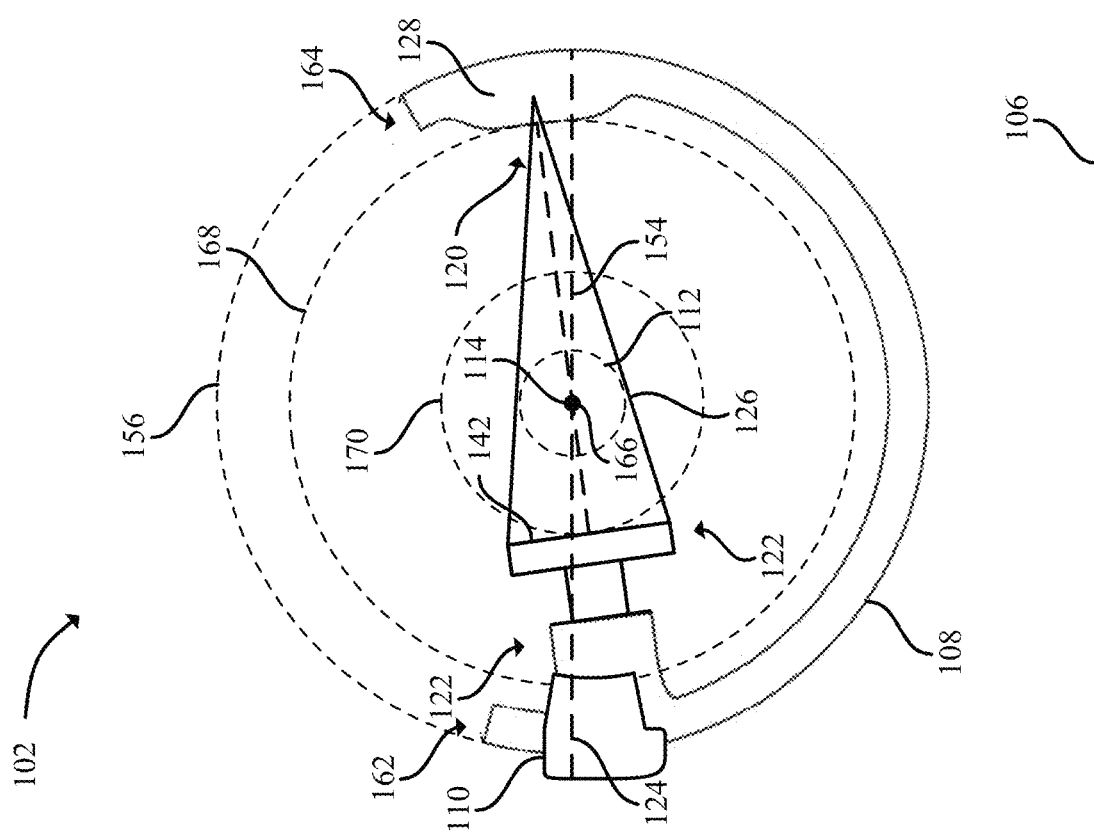
FIG. 6 is a schematic diagram of a C-arm of a medical imaging system in a third position in accordance with an exemplary embodiment.
Figure 5:
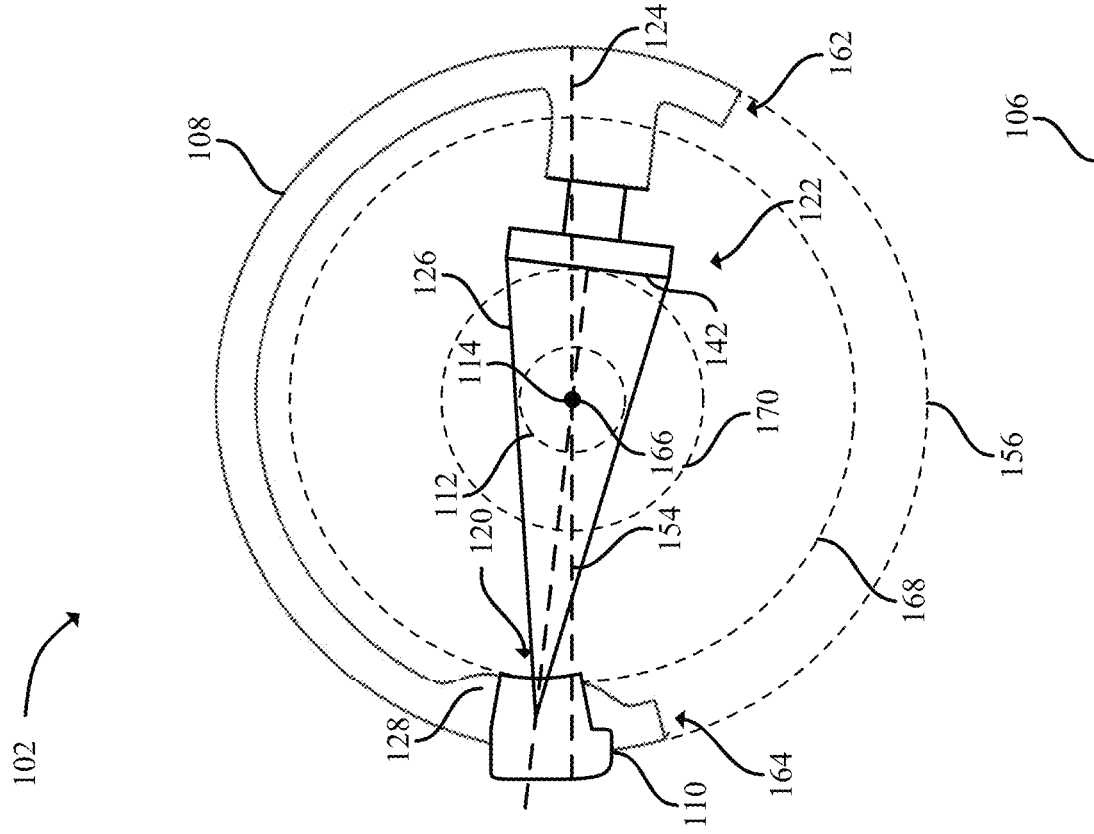
FIG. 5 is a schematic diagram of a C-arm of a medical imaging system in a second position in accordance with an exemplary embodiment.

For example, the computing device 144 may send a signal to the C-arm motor controller 138 which causes the C-arm motor controller 138 to rotate the C-shaped portion 108. Referring collectively to FIGS. 4-6, various example positions of the C-arm 102 are shown. In FIGS. 4-6, the base 104 and the cable 134 have been omitted and in FIGS. 5 and 6 the outlet 130 has also been omitted for clarity.

Figure 2:
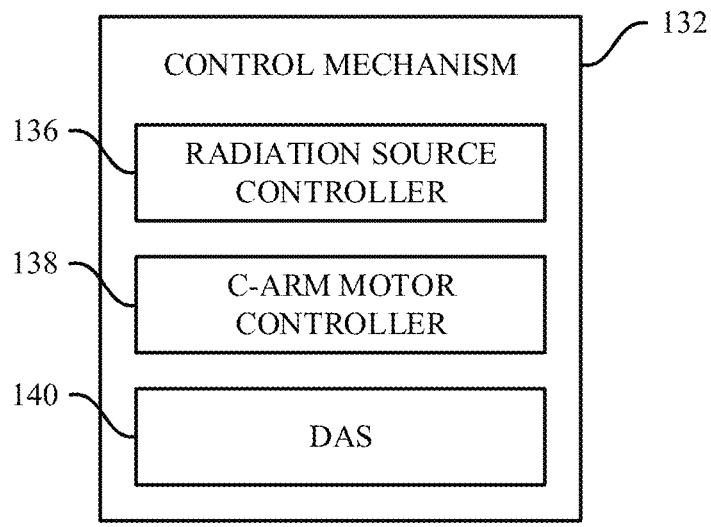
FIG. 2 is a block diagram of a control mechanism of a medical imaging system in accordance with an exemplary embodiment.

Specifically, FIG. 4 shows the C-arm 102 in a first position in which the axis 124 between the detector surface 142 and the outlet 130 is arranged perpendicular to the ground surface 106 on which the medical imaging system 100 sits. Furthermore, as depicted in FIGS. 1 and 2, in the first position, the axis 124 is perpendicular to a horizontal axis 154. The horizontal axis 154 is parallel to the ground surface 106. FIG. 5 depicts the C-arm 102 in a second position in which the C-arm shaped portion 108 has been rotated. In the second position, the radiation source 120 is positioned closer to the extended portion 110 and the radiation detector 122 is positioned further from the extended portion 110 relative to the first position as shown by FIG. 4. FIG. 6 depicts the C-arm 102 in a third position in which the C-shaped portion 108 has been rotated. In the third position, the radiation source 120 is positioned further from the extended portion 110 and the radiation detector 122 is positioned closer to the extended portion 110 relative to the first position as shown by FIG. 4.

A rotational range of the C-shaped portion (i.e., an amount of angle through which the C-shaped portion 108 may rotate relative to the base 104) may be greater than 180° (i.e., 200°, 205°, 220°, etc.). For example, FIG. 5 may correspond to a rotation of the C-shaped portion 108 by an angle of approximately 95° around the rotational axis 114 relative to the position shown by FIG. 4, and FIG. 6 may correspond to a rotation of the C-shaped portion 108 by an angle of approximately −95° around the rotational axis 114 relative to the position shown by FIG. 4, with the C-shaped portion 108 rotating through 190° to adjust from the position shown by FIG. 6 to the position shown by FIG. 5. In each of FIGS. 2-4, the extended portion 110 is maintained in position relative to the C-shaped portion 108, with the position of extended portion 110 in FIGS. 4-6 being the same as the position of extended portion 110 shown in FIG. 1 (i.e., with the extended portion 110 not rotated relative to the ground surface 106 or horizontal axis 154).

The radiation source 120 emits the radiation 126 towards the radiation detector 122. As the C-shaped portion 108 rotates around the rotational axis 114 (i.e., while imaging the patient 118), the radiation 126 remains directed toward the radiation detector 122 due to the concurrent rotation of each of the radiation source 120 and the radiation detector 122 around the rotational axis 114. While rotating around the rotational axis 114, the C-shaped portion 108 may move along path 156 in a first direction 158 or a second direction 160. Since the radiation source 120 and the radiation detector 122 rotate around the rotational axis 114 with the C-shaped portion 108, the radiation 126 emitted by the radiation source 120 passes through the examination region 112.

While stationary or rotating, a first end 162 and a second end 164 of the C-shaped portion 108 are positioned a same distance from a center 166 of the C-shaped portion 108. The center 166 of the C-shaped portion 166 shares a same position as the rotational axis 114. For example, the C-shaped portion 108 may have a uniform radius of curvature in a direction around the center 166 (i.e., a same radius of curvature at each location along the C-shaped portion 108 in the direction around the center 166) such that the first end 162 and the second end 164 are positioned a same distance from the center 166 of the C-shaped portion 108 along the axis 124. As such, the path 156 has a same curvature and radius as the C-shaped portion 108.

As described above, the C-shaped portion 108 may rotate around the rotational axis 114. In some embodiments, C-shaped portion 108 may also rotate about horizontal axis 154. In this configuration, the C-shaped portion 108 may rotate around either of rotational axis 114 or horizontal axis 154 (or both of rotational axis 114 and horizontal axis 154), where horizontal axis 154 is orthogonal to the rotational axis 114. In the views shown by FIGS. 4-6, however, the C-shaped portion 108 is rotated only around the rotational axis 114 and not the horizontal axis 154.

Although the first end 162 and second end 164 may be positioned the same length from the center 166, each of outlet 130 and detector surface 142, may be positioned at different lengths from the center 166 since the position of the detector 122 may be varied. For example, a rotational path 168 of the outlet 130 and a rotational path 170 of the radiation detector surface 142 may be different, with each of rotational path 168 and rotational path 170 being of circular shape. The outlet 130 may move along rotational path 168 and detector surface 142 may move along rotational path 170 during conditions in which the C-shaped portion 108 is rotated around rotational axis 114 (i.e., while the patient 118 is being imaged). However, a length 172 (i.e., a diameter of the rotational path 168) may be a longer length from the center 166 to the outlet 130 than a length 174 (i.e., a diameter of the rotational path 170) from the center 166 to the detector surface 142. In one embodiment, the length 172 may be larger than the length 174 due to the radiation source 120 being seated within the C-shaped portion 108. For example, in the embodiment depicted in FIG. 4, the radiation source 120 includes an X-ray tube 176. In this embodiment, the X-ray tube 176 may be housed within casing 128 and seated within the C-shaped portion 108. For the sake of clarity, the X-ray tube 176 has been omitted in FIGS. 5 and 6.

Positioning the X-ray tube 176 within the C-shaped portion 108 may enable the outlet 130 to be positioned closer to the second end 164 compared to configurations in which an X-ray tube 176 is not seated within the C-shaped portion 108, which may result in a decreased height of the radiation source 120 as a height of the radiation source 120 may be limited by the casing 128. The resulting reduced height of the radiation source 120 may increase an amount of open space between the detector surface 142 and the outlet 130, which may enable the C-arm 102 to accommodate larger patients and/or increase ease of use of the C-arm 102. Furthermore, in some embodiments, the seated position of the radiation source 120 within the C-shaped portion 108 may increase a balance of the C-arm 102, which may reduce undesired vibration of the C-arm 102. Positioning the radiation source 120 within the C-shaped portion 102 may also increase a balance of the C-arm 102 while the C-shaped portion 108 is rotating (i.e., while the patient 118 is being imaged) and may provide a counter weight to the radiation detector 122 which may reduce a load and/or vibration of a motor of the medical imaging system 100.

Returning to FIG. 1, in one embodiment, the medical imaging system 100 includes, or is coupled to a picture archiving and communication system (PACS). In an exemplary implementation, the PACS may be further coupled to a remote system such as a radiology department information system, hospital information system, an internal and/or an external network, etc. to allow operators at different locations to supply commands, parameters, and/or gain access to image data generated by the medical imaging system 100.

The medical imaging system 100 further includes or is coupled to an image reconstructor. As previously noted, the DAS 140 samples and digitizes projection data acquired by the radiation detector 122. Subsequently, the image reconstructor uses the sampled and digitized X-ray data to perform high-speed reconstruction. In certain embodiments, the image reconstructor may form part of the computing device 144. Alternatively, the image reconstructor may be omitted and instead the computing device 144 may perform one or more functions of the image reconstructor. Moreover, the image reconstructor may be located locally or remotely and may be operatively coupled to the medical imaging system 100 via a wired or wireless network. Particularly, in one embodiment, the reconstructor may use computing resources in a "cloud" network cluster for image reconstruction.

In some embodiments the reconstructor receives projection data and the projection data undergoes preprocessing and calibration to condition the data to represent the line integrals of attenuation coefficients of the patient 118. The processed data is commonly referred to as "projections." The acquired sets of projection data may be used for basis material decomposition (BMD). During BMD, the measured projections are converted to a set of material-density projections. The material-density projections may be reconstructed to form a pair or set of material-density maps or images of each respective basis material (i.e., bone, tissue, and/or contrast agents, etc.). The density maps or images may be, in turn, associated to form a volume rendering of the basis material in the imaged volume.

The projection data is processed to reconstruct an image that corresponds to a two-dimensional slice taken through the patient 118, or in some examples wherein the projection data includes multiple vies or scans, a three-dimensional rendering of a portion of the patient 118. Once reconstructed, a basis material image reveals internal features of the patient 118 expressed by the densities of the materials. The image may be displayed to show these features. Once displayed, a practitioner may view the image to make a medical diagnosis or to discern characteristics of a feature of interest (i.e., lesion, organ, etc.).

As used herein, the phrase "reconstructing an image" is not intended to exclude embodiments in which data representing an image is generated but a viewable image is not. Therefore, as used herein, the term image broadly refers to both viewable images and data representing a viewable image. However, some embodiments described herein generate (or are configured to generate) at least one viewable image.

In one embodiment, the reconstructor stores reconstructed images in the system memory 148. In another embodiment, the reconstructor transmits the reconstructed image(s) to the computing device 144 for generating useful patient information for diagnosis and evaluation. In certain embodiments, the computing device 144 may transmit reconstructed images and/or patient informant to the display 150. In other embodiments, the reconstructed images may be transmitted from the system memory 148 or the reconstructor to the PACS for short-term or long-term storage.

Figure 7:
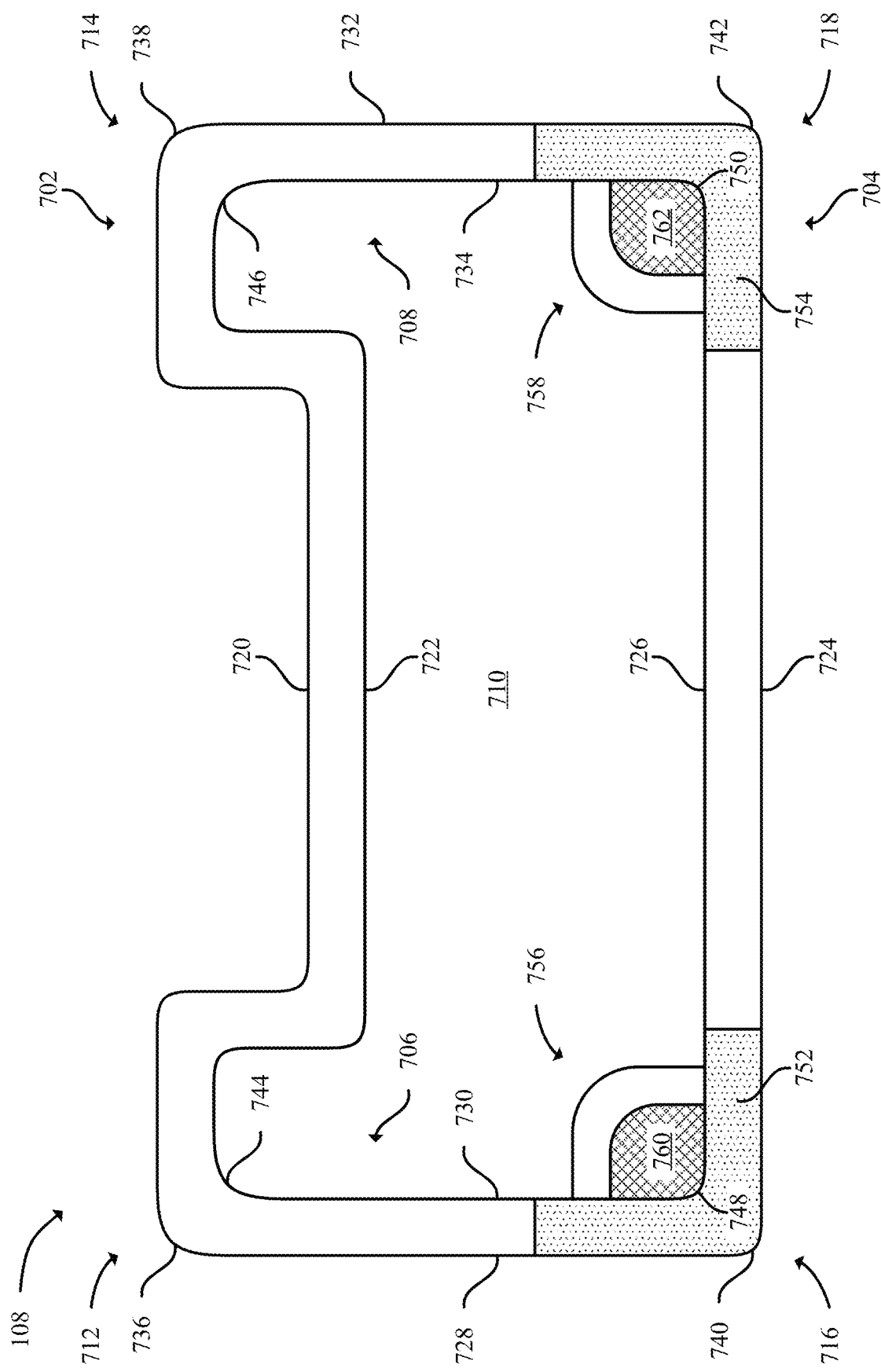
FIG. 7 is a cross sectional view of a C-arm of a medical imaging system in accordance with an exemplary embodiment.

Referring now to FIG. 7, a cross sectional view of the C-shaped portion 108 is shown in accordance with an exemplary embodiment. The C-shaped portion 108 includes first end wall 702 and a second end wall 704 that is opposite the first end wall 702. The first end wall 702 is further from the center 166 of the C-shaped portion 108 than the second end wall 704. The C-shaped portion 108 further includes a first side wall 706 and a second side wall 708 that is opposite the first side wall 706. The first side wall 706 and the second side wall 708 extend between the first end wall 702 and the second end wall 704. The first end wall 702, the second end wall 704, the first side wall 706, and the second side wall 708 define an interior cavity 710 of the C-shaped portion 108.

The first end wall 702 and the second end wall 704 extend between the first side wall 706 and the second side wall 708. The first end wall 702 meets the first side wall 706 at a first joint 712 and meets the second side 708 wall at a second joint 714. The second end wall 704 meets the first side wall 706 at a third joint 716 and meets the second side wall 708 at a fourth joint 718.

The first end wall 702 includes an outer surface 720 and an inner surface 722 that is opposite the outer surface 720, the second end wall 704 includes an outer surface 724 and an inner surface 726 that is opposite the outer surface 724, the first side wall 706 includes an outer surface 728 and an inner surface 730 that is opposite the outer surface 728, and the second side wall 708 includes an outer surface 732 and an inner surface 734 that is opposite the outer surface 732. Each of the outer surfaces 720, 724, 728, and 732 face away from the cavity 710 while each of the inner surfaces 722, 726, 730, and 734 face towards cavity 710. While FIG. 7 depicts the outer surface 710 as including a recessed portion, in other embodiments the recessed portion may be omitted and the outer surface 710 may be a flush surface.

The outer surface 720 extends between the outer surfaces 728 and 732. The outer surface 720 meets the outer surface 728 at a first outer joint 736 and meets the outer surface 732 at a second outer joint 738. The outer surface 724 extends between the outer surfaces 728 and 732. The outer surface 724 meets the outer surface 728 at a third outer joint 740 and metes the outer surface 732 at a fourth outer joint 742. The inner surface 722 extends between the inner surfaces 730 and 734. The inner surface 722 meets the inner surface 730 at a first inner joint 744 and meets the inner surface 734 at a second inner joint 746. The inner surface 726 extends between the inner surfaces 730 and 734. The inner surface 726 meets the inner surface 730 at a third inner joint 748 and meets the inner surface 734 at a fourth inner joint 750. The first joint 712 includes the first outer joint 736 and the first inner joint 744, the second joint 714 includes the second outer joint 738 and the second inner joint 746, the third joint 716 includes the third outer joint 740 and the third inner joint 748 and the fourth joint 718 includes the fourth outer joint 742 and the fourth inner joint 750.

At least a portion of the first end wall 702, the second end wall 704, the first side wall 706, and/or the second side wall 706 is formed of a carbon fiber material (i.e., a carbon fiber fabric). In one embodiment the first end wall, 702, the second end wall 704, the first side wall 706, and the second side wall 706 is completely composed of a carbon fiber material. In this embodiment, the entire C-shaped portion 108 is composed of a carbon fiber material. In some embodiments, each layer of carbon fiber fabric that forms the carbon fiber material of at least one of the first end wall 702, the second end wall 704, the first side wall 706, and/or the second side wall 706 has a thickness of 4.8 mm. In this embodiment, the carbon fiber material includes 16 layers of carbon fiber fabric. Each layer may have a 45° orientation with respect to a preceding and/or a subsequent layer of carbon fiber fabric. Forming the C-shaped portion 108 with carbon fiber material may increase a total strength of the C-shaped portion 108 which may allow the C-shaped portion 108 to support approximately 100 KG of payload. In some embodiments, the C-shaped portion 108 may support 50 KG of payload at the first end 162 and the second end 164.

When the medical imaging system 100 is acquiring a medical image (i.e., when the radiation source 120 is emitting radiation), stress may be placed on the C-shaped portion 108 due to the forces produced by the radiation source 120 and the forces associated with a rotation of the C-shaped portion 108. The stress placed on the C-shaped portion 108 may cause the C-arm 102 to vibrate. This vibration may produce undesirable image artifacts within a medical image captured by the medical imaging system 100. These forces may not be uniformly distributed throughout the C-shaped portion 108. Stated otherwise, some regions of the C-shaped portion 108 may experience more stress than other regions of the C-shaped portion 108.

As shown in FIG. 7, the C-shaped portion 108 includes a first region 752 and a second region 754 that is opposite the first region 752. The first region 752 and the second region 754 may experience more stress than a remainder of the C-shaped portion 108. The first region 752 includes at least the third joint 716 and in some embodiments, as depicted in FIG. 7, includes a portion of the first side wide wall 706 and the second end wall 704. The second region includes at least the fourth joint 718 and, in some embodiments, as depicted in FIG. 7 includes a portion of the second side wall 708 and the second end wall 704. In some embodiments, the first region 752 and the second region 754 may be formed of a unidirectional ultra-high modulus carbon fiber material. A unidirectional carbon fiber material may include a plurality of layers of carbon fiber fabric oriented in a same direction. Stated another way, a unidirectional carbon fiber material may include a plurality of parallel layers of carbon fiber fabric. A high modulus carbon fiber material may include a plurality of layers of carbon fiber fabric with a rating of at least 33 million pounds per square inch (MSI). As such, a unidirectional ultra-high modulus carbon fiber material may include a plurality of parallel layers of carbon fiber fabric wherein each layer has at least a 65 MSI (or approximately 440 Gpa) rating.

Figure 8:
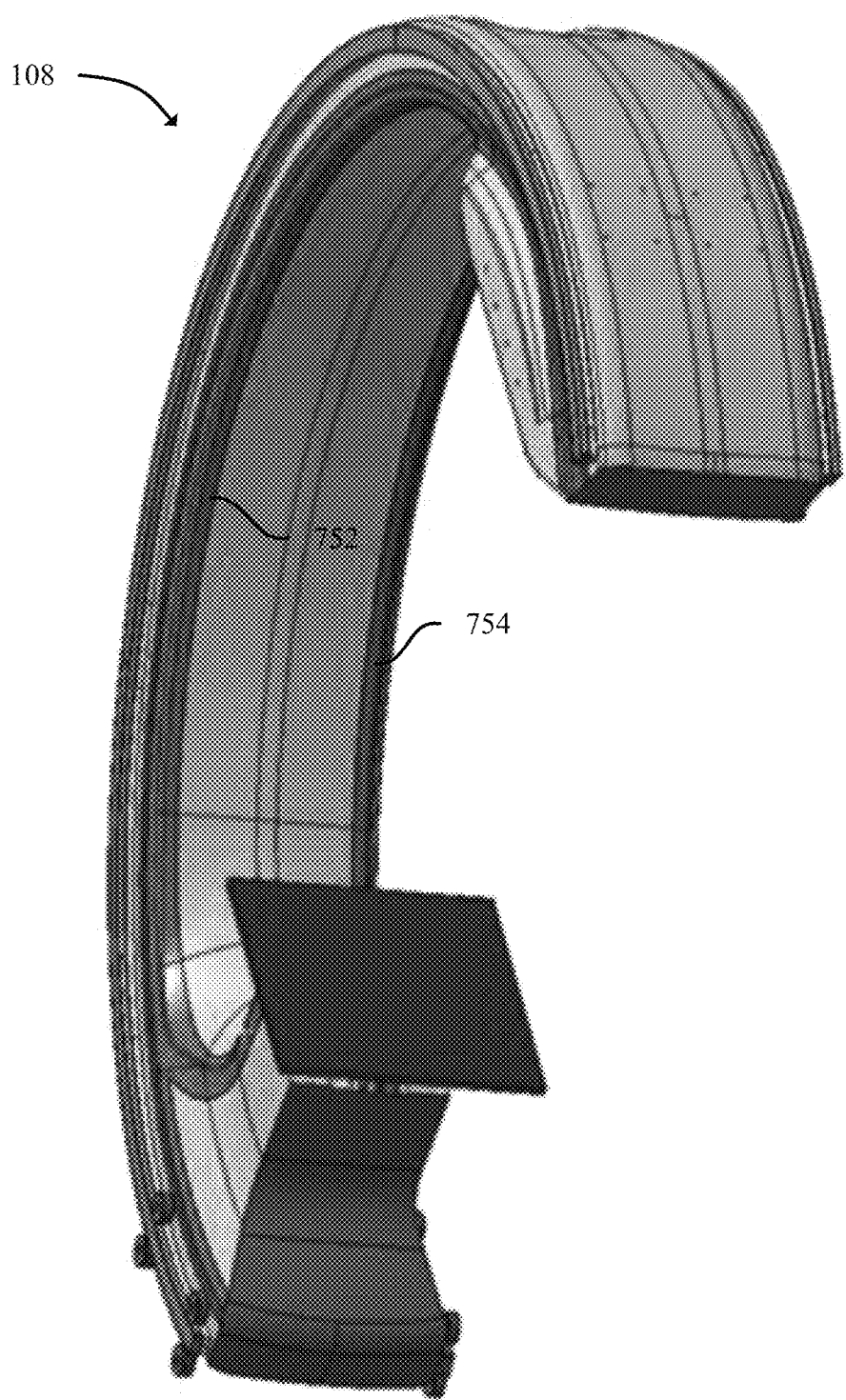
FIG. 8 depicts a C-arm of a medical imaging system in accordance with an exemplary embodiment.

Briefly turning to FIG. 8, the C-shaped portion 108 is further depicted in accordance with an exemplary embodiment. As shown in FIG. 8, the first region 752 and the second region 754 extends throughout the C-shaped portion 108. In FIG. 8, the first region 752 and the second region 754 are shown as darker gray with respect to the remainder of the C-shaped portion 108. A majority of the first region 752 and the second region 754 extends along an inner radius of the C-shaped portion 108. Furthermore, as depicted in FIG. 8, the first region 752 and the second region 754 further extend towards the radiation detector 122.

Returning now to FIG. 7, the C-shaped portion 108 may further include a first reinforcement 756 and a second reinforcement 758 that is opposite the first reinforcement 756. While first reinforcement 756 and the second reinforcement 758 are shown as rounded structures, in another embodiment, the first reinforcement 756 and the second reinforcement 758 may be shaped as 45° chamfers. The first reinforcement 756 and the second reinforcement 758 are located within the cavity 710. The first reinforcement 756 extends from the first side wall 706 and extends from the second end wall 704. Stated another way, the first reinforcement 748 extends from the inner surface 730 of the first side wall 706 and extends from the inner surface 726 of the second end wall 704. The first reinforcement 756 covers the third inner joint 748. In some embodiments, the first reinforcement 756 is adjacent to the first region 752 throughout the C-shaped portion 108. The second reinforcement 758 extends from the second side wall 708 and extends from the second end wall 704. Stated another way, the second reinforcement 758 extends from the inner surface 734 of the second side wall 708 and extends from the inner surface 726 of the second end wall 704. The second reinforcement covers the fourth inner joint 750. In some embodiments, the second reinforcement 758 is adjacent to the second region 754 throughout the C-shaped portion 108.

The first reinforcement 756 includes an inner region 760 and the second reinforcement 758 includes an inner region 762. At least a portion of the inner region 760 is adjacent to the third inner joint 748 and at least a portion of the inner region 762 is adjacent to the fourth inner joint 750. The inner region 760 and the inner region 762 may be formed of a unidirectional ultra-high modulus carbon fiber material. In one embodiment, the first reinforcement 756 and the second reinforcement 758 may be formed of sixteen layers of carbon fiber fabric. In this embedment, eight of the layers (i.e., the eight middle layers) may be formed of a unidirectional ultra-high modulus carbon fiber fabric. As such, at least a portion of the first reinforcement 756 and the second reinforcement 758 may be formed of a high module carbon fiber material.

Forming the first region 752, the second region 754, the first reinforcement 756, and the second reinforcement 758 of a unidirectional ultra-high modulus carbon fiber material may strengthen the first region 752 and the second region 754 and therefore may increase the overall strength of the C-shaped portion 108. Strengthening the first region 752 and the second region 754 may also reduce an amount of vibration the C-shaped portion 108 experiences.

Figure 9:
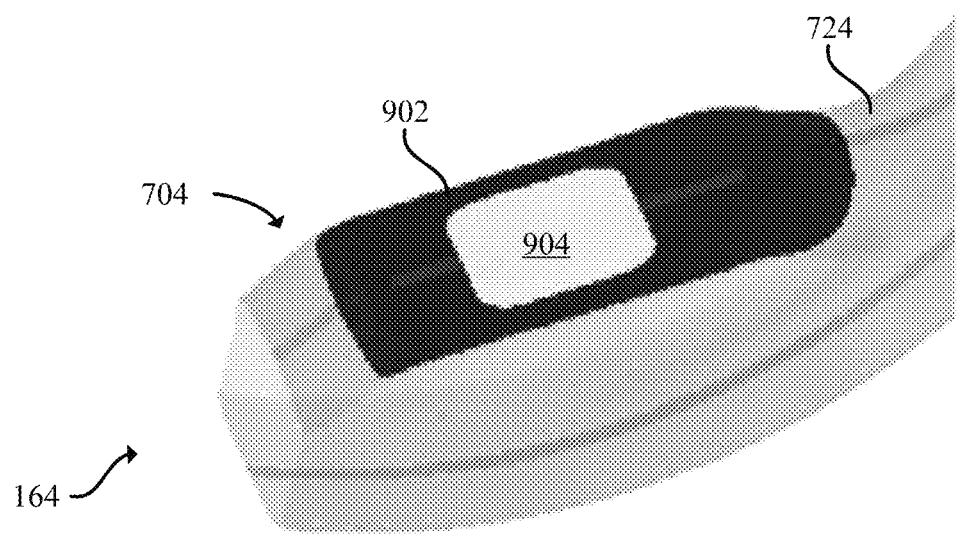
FIG. 9 depicts an end of a C-arm of a medical imaging system with a removeable cover in accordance with an exemplary embodiment.

Referring now to FIG. 9, an elevated view of the second end 164 is shown in accordance with an exemplary embodiment. As previously discussed, in some embodiments, the radiation source 120 may be seated within the C-shaped portion 108. Accordingly, a portion of the outer wall 704 may define an opening shaped to receive the radiation source 102 thereby placing the radiation source 120 within the cavity 710. After placing the radiation source 102 within the cavity 710, it is desirable for the radiation source 120 to remain accessible for maintenance purposes.

Figure 10:
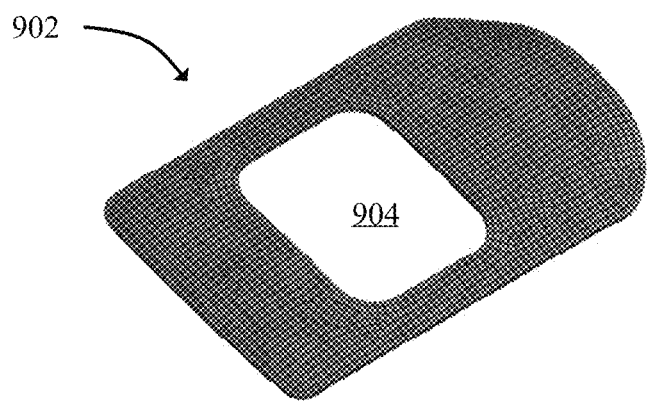
FIG. 10 depicts a removeable cover of a C-arm of a medical imaging system in accordance with an exemplary embodiment.

As shown in FIGS. 9 and 10, in some embodiments, the C-shaped portion 108 may include a cover 902 that covers an opening of the C-shaped portion 108 that is vertically above the radiation source 120 when the C-shaped portion 108 is in the first position as depicted in FIG. 1. The cover 902 rests upon and is removably attached to the outer surface 724 of the second end wall 704 and has a shape that corresponds to a shape of an opening of the C-shaped portion 108. The cover 902 defines an opening 904. The opening 904 defines the outlet 130. As such, the radiation 126 passes through the opening 904 after being emitted by the radiation source 120. In some embodiments, the cover 902 may be formed of a carbon fiber material that includes 16 layers of carbon fiber fabric. Providing a cover 902 that is formed of a carbon fiber material may further reduce the weight of the C-shaped portion 108 which may further increase a durability of the C-shaped portion 108. FIG. 10 further depicts the cover 902 removed from the C-shaped portion 108. Forming the cover 902 of a carbon fiber material provides additional stiffness to the C-shaped portion 108.

Figure 11:
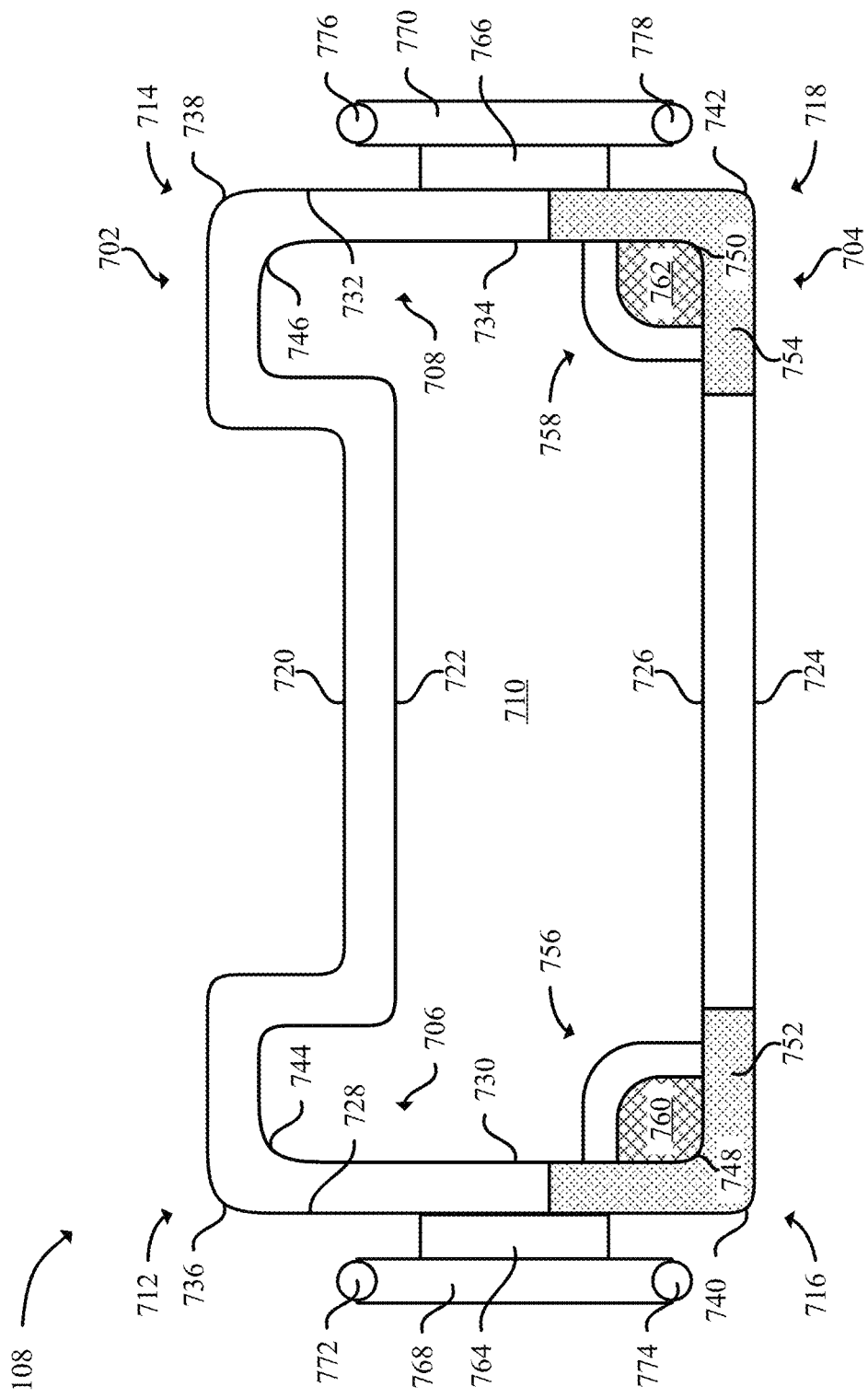
FIG. 11 is a cross sectional view of a C-arm of a medical imaging system in accordance with an exemplary embodiment.

Referring now to FIG. 11, an embodiment of the C-shaped portion 108 is shown in accordance with an exemplary embodiment. In this embodiment, the C-shaped portion includes a first extension 764 and a second extension 766. The first extension 764 extends perpendicular from the first side wall 706 and the second extension 766 extends perpendicular from the second side wall 708. Stated another way, the first extension 764 extends perpendicular from the outer surface 728 of the second first wall 706 and the second extension 766 extends perpendicular form the outer surface 732 of the second side wall 708. The first extension 764 and the second extension 766 may be formed of a nondeformable material.

The C-shaped portion 108 further includes a first rod support 768 and a second rod support 770. The first rod support 768 extends from the first extension 764 and the second rod support 770 extends from the second extension 766. The first rod support 768 supports and is coupled to a first rod 772 and a second rod 774 and the second rod support 770 supports and is coupled to a third rod 776 and a fourth rod 778. The rod supports 768 and 770 and the rods 772-778 may be formed of structural steel.

Figure 12:
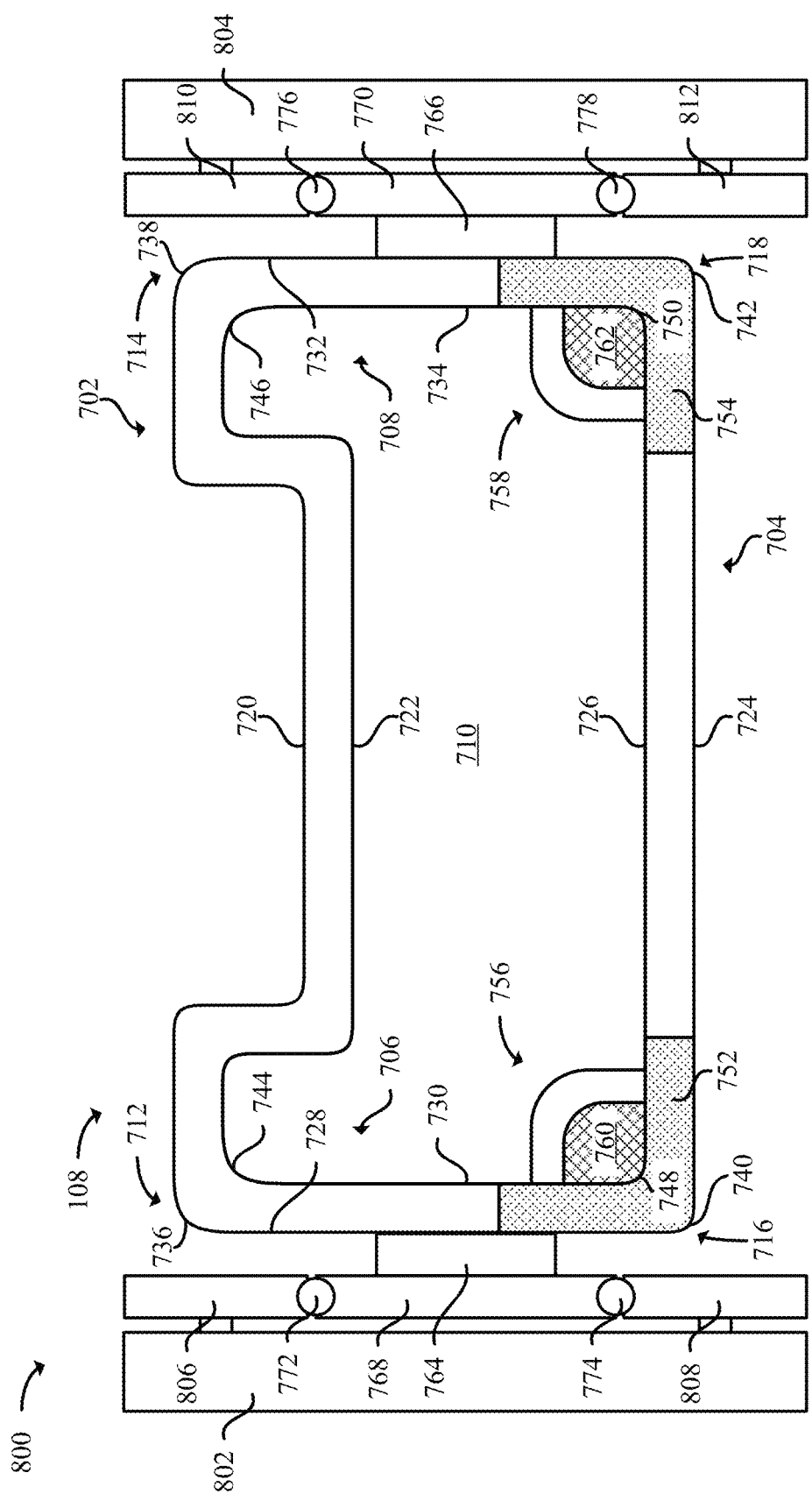
FIG. 12 is a cross sectional view of a C-arm of a medical imaging system coupled to a guide system of the medical imaging system in accordance with an exemplary embodiment.

Referring now to FIG. 12, a guide system 800 coupled the C-shaped portion 108 is shown in accordance with an exemplary embodiment. As described above, the guide system 800 may rotate the C-shaped portion via a coupling between the C-shaped portion 108 and the guide system 800. The guide system 800 is located within the extended portion 110 and includes a first trolley 802 and a second trolley 804.

The guide system 800 further includes a first roller 806, a second roller 808, a third roller 810 and a fourth roller 812. While FIG. 12 depicts four rollers, in some embodiments, the guide system may include more rollers. For example, in another embodiment, each roller 806-812 may be one of two rollers that are immediately next to one another. As such, in this example, the guide system 800 includes eight rollers. The first roller 806 and the second roller 808 extend from and are supported by the first trolley 802. The third roller 810 and the fourth roller 812 extend from and are supported by the second trolley 804. The first roller 806 is adjacent to the first rod 772, the second roller 808 is adjacent to the second rod 774, the third roller 810 is adjacent to the third rod 776, and the fourth roller 812 is adjacent to the fourth rod 778. When the C-shaped portion 108 rotates, the rollers 806-812 rotate about the rods 772-778 respectively (i.e., the first roller 806 rotates about the first rod 772) thereby causing C-shaped portion 108 to translate in a given rotational direction.

Figure 13:
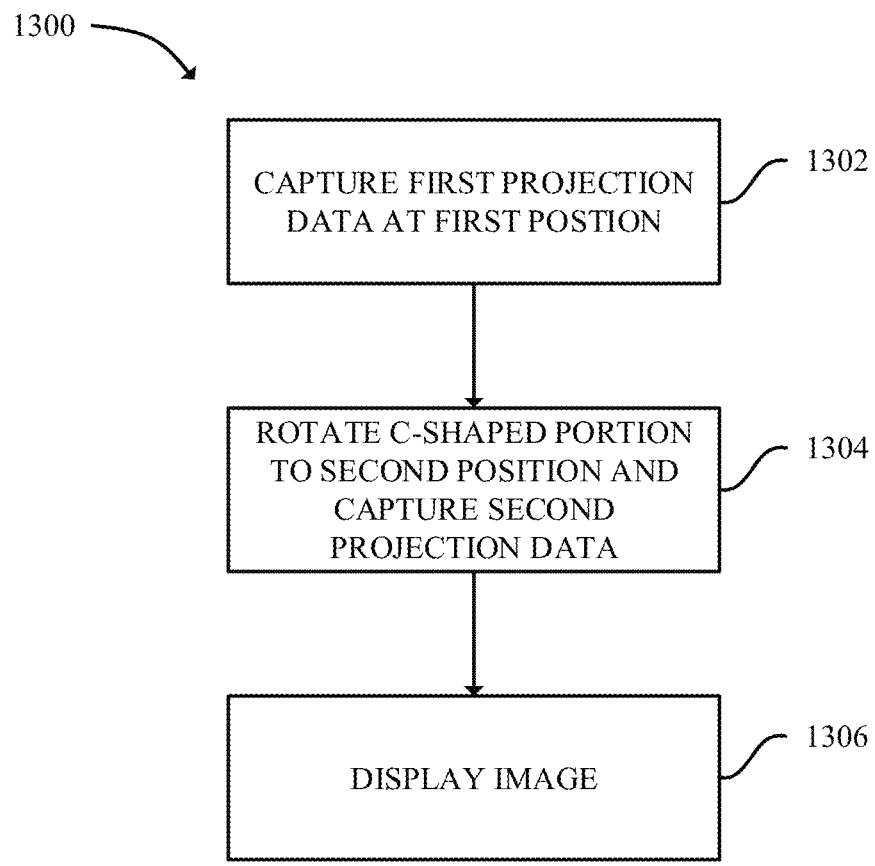
FIG. 13 is a flow chart of a method for imaging a patient with a medical imaging system in accordance with an exemplary embodiment.

Turning to FIG. 13, a method 1300 for imaging a patient with the medical imaging system 100 is shown in accordance with an exemplary embodiment. Various aspects of the method 1300 depicted in FIG. 13 may be carried out by a "configured processor." As used herein, a configured processor is a processor that is configured according to an aspect of the present disclosure. In some embodiments, the processor 146 is a configured processor(s). The computer readable program instructions, that when executed by a configured processor, cause a configured processor to carry out the steps of the method 1300 are stored in a computer readable storage medium, including, but not limited to, the system memory 148.

At 1302, a configured processor sends a first signal to begin medical image acquisition to the control mechanism 132. In response to receiving the first signal to begin medical image acquisition, the control mechanism 132 causes the medical imaging system 100 to begin acquiring first projection data of the patient 118 while the C-shaped portion is at a first position as previously described herein. In one embodiment, the configured processor sends the signal to begin medical image acquisition in response to a user selecting an imaging protocol and/or a start icon or the like displayed in a GUI that is shown by the display 150. Furthermore, the signal to begin medical image acquisition includes imaging parameters (i.e., radiation source power and timing parameters, C-arm rotational speed and position parameters, etc.). In response to receiving the first signal to begin medical image acquisition, the control mechanism 132 controls the position of the C-arm 102 and the operation of the radiation source 120 as a function of the received parameters which causes the medical imaging system 100 to acquire projection data of an internal region of interest (i.e., organ, bone, tissue, etc.) of the patient 118.

At 1304, the configured processor sends a second signal to begin medical image acquisition to the control mechanism 132. In response to receiving the second to begin medical image acquisition, the control mechanism 132 causes the C-shaped portion 108 to rotate to a second position and causes the medical imaging system 100 to begin acquiring second projection data of the patient 118 while the C-shaped portion is at a second position as previously described herein. In one embodiment, the configured processor sends the second signal to begin medical image acquisition in response to a user selecting an imaging icon or the like displayed in a GUI that is shown by the display 150. In another embodiment, the configured processor automatically sends the second signal based on an imaging protocol.

At 1306, the configured processor reconstructs an image from at least one of the first and second projection data as previously discussed herein and sends the reconstructed image to the display 150. In response to receiving the reconstructed image, the display 150 displays the image.

In addition to any previously indicated modification, numerous other variations and alternative arrangements may be devised by those skilled in the art without departing from the spirt and scope of this description, and appended claims are intended to cover such modifications and arrangements. Thus, while the information has been described above with particularity and detail in connection with what is presently deemed to be the most practical and preferred aspects, it will be apparent to those of ordinary skill in the art that numerous modifications, including, but not limited to, form, function, manner of operation, and use may be made without departing from the principles and concepts set forth herein. Also, as used herein, the examples and embodiments are meant to be illustrative only and should not be construed to be limiting in any manner

What is claimed is:

1. A C-shaped arm for use with a medical imaging system comprising:
   a C-shaped portion;
   a radiation source carried by the C-shaped portion; and
   a radiation detector carried by the C-shaped portion,
      wherein at least a portion of the C-shaped portion is formed of a unidirectional ultra-high modulus carbon fiber material.

2. The C-shaped arm of claim 1, wherein a remainder of the C-shaped portion is formed of a different carbon fiber material.

3. The C-shaped arm of claim 1, wherein the C-shaped portion comprises:
   a first region formed of unidirectional ultra-high modulus carbon fiber material; and
   a different second region formed unidirectional ultra-high modulus carbon fiber material.

4. The C-shaped portion of claim 3, wherein the first region and the second region extend about an inner radius of the C-shaped portion.

5. The C-shaped arm of claim 3, wherein the first region includes a first joint of the C-shaped portion and the second region includes a different second joint of the C-shaped portion.

6. The C-shaped arm of claim 3, wherein the C-shaped portion further comprises:
   a third region extending between the first region and the second region, wherein the third region is formed of a different carbon fiber material.

7. The C-shaped arm of claim 1, wherein the unidirectional ultra-high modulus carbon fiber material is located within a cavity of the C-shaped portion.

8. The C-shaped portion of claim 7, wherein the C-shaped portion comprises:
   a first reinforcement within the cavity and adjacent to a first inner joint of the C-shaped portion;
   a second reinforcement within the cavity and adjacent to a second inner joint of the C-shaped portion,
      wherein the first reinforcement and the second reinforcement are formed of a unidirectional ultra-high modulus carbon fiber material.

9. The C-shaped arm of claim 1, wherein the radiation source is within a cavity of the C-shaped portion and further comprising:
   a removable cover formed of a carbon fiber material, wherein the removable cover defines a radiation outlet for radiation emitted by the radiation source.

10. A medical imaging system comprising:
    a C-arm;
    a radiation source and a radiation detector carried by the C-arm;
    a base;
    an extended portion coupled to the C-arm and the base, wherein the C-arm is configured at least 220° about an examination region.

11. The medical imaging system of claim 10, wherein at least a portion of the C-arm is formed of a carbon fiber material.

12. The medical imaging system of claim 11, wherein the carbon fiber material is a unidirectional ultra-high modulus carbon fiber material.

13. The medical imaging system of claim 11, wherein C-arm comprises:
    a first region formed of unidirectional ultra-high modulus carbon fiber material; and
    a different second region formed unidirectional ultra-high modulus carbon fiber material.

14. The medical imaging system of claim 13, wherein the first region and the second region extend about an inner radius of the C-shaped arm.

15. The medical imaging system of claim 10, wherein the portion of the C-arm that is formed of a carbon fiber material is located within a cavity of the C-shaped arm.

16. The medical imaging system of claim 10, wherein the C-arm is formed of a of a unidirectional ultra-high modulus carbon fiber material and a different carbon fiber material.

17. The medical imaging system of claim 16, wherein the C-arm further comprises:
    a first reinforcement within a cavity of the C-arm and adjacent to a first inner joint of the C-arm; and
    a second reinforcement within the cavity and adjacent to a second inner joint of the C-arm,
       wherein the first reinforcement and the second reinforcement are formed of the unidirectional ultra-high modulus carbon fiber material.

18. The medical imaging system of claim 10, wherein the radiation source is within a cavity of the C-arm and the C-arm further comprises:
    a removable cover formed of a carbon fiber material, wherein the removable cover defines a radiation outlet for radiation emitted by the radiation source.

19. A method comprising:
    acquiring first projection data with a medical imaging system that includes a C-arm that carries a radiation source and a detector, wherein the C-arm is at a first position when the medical imaging system acquires the first projection data,
       wherein a portion of the C-arm is formed of a unidirectional ultra-high modulus carbon fiber material;
    rotating the C-arm to a second position;
    acquiring second projection data with the medical imaging system when the C-arm is at the second position;
    reconstructing an image form at least one of the first projection data and the second projection data; and
    displaying the reconstructed image.

20. The method of claim 19, wherein the portion of the C-arm formed of the unidirectional ultra-high modulus carbon fiber material is located within a cavity of the C-arm.

* * * * *